US012623013B2

(12) United States Patent
Tao et al.

(10) Patent No.: US 12,623,013 B2
(45) Date of Patent: May 12, 2026

(54) COMPOUNDS, SYSTEMS, AND TECHNIQUES FOR REMOVAL OF PERIPHERAL AMYLOID BETA PEPTIDE WITH ALBUMIN BINDING COMPETITORS

(71) Applicant: Fresenius Medical Care Holdings, Inc., Waltham, MA (US)

(72) Inventors: Xia Tao, Waltham, MA (US); Peter Kotanko, Waltham, MA (US); Stephan Thijssen, Waltham, MA (US); Vaibhav Maheshwari, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 610 days.

(21) Appl. No.: 18/083,827

(22) Filed: Dec. 19, 2022

(65) Prior Publication Data

US 2023/0201438 A1 Jun. 29, 2023

Related U.S. Application Data

(60) Provisional application No. 63/293,122, filed on Dec. 23, 2021.

(51) Int. Cl.
*A61M 1/16* (2006.01)
*A61M 1/34* (2006.01)
*A61M 1/36* (2006.01)

(52) U.S. Cl.
CPC ............ *A61M 1/3486* (2014.02); *A61M 1/16* (2013.01); *A61M 1/1676* (2014.02);
(Continued)

(58) Field of Classification Search
CPC .... A61M 1/16; A61M 1/1676; A61M 1/3403; A61M 1/3413; A61M 1/342;
(Continued)

(56) References Cited

U.S. PATENT DOCUMENTS 8,206,591 B2    6/2012  Kotanko
8,419,943 B2    4/2013  Kotanko
                (Continued)

FOREIGN PATENT DOCUMENTS

WO      2004056318 A2    7/2004
WO      2011095545 A1    8/2011
WO      2021155142 A1    8/2021

OTHER PUBLICATIONS

Adams et al., "Extending the half-life of a fab fragment through generation of a humanized anti-human serum albumin Fv domain: An investigation into the correlation between affinity and serum half-life," MAbs. 8(7):1336-1346 (2016).
(Continued)

*Primary Examiner* — John Kim
(74) *Attorney, Agent, or Firm* — KDW Firm PLLC

(57) ABSTRACT

Compounds, systems, kits, methods, and/or apparatuses may be operative to reduce amyloid beta (Aβ) peptide in a patient, including a central nervous system (CNS) of the patient and/or a periphery (non-CNS portion) of the patient. In some embodiments, a displacer fluid comprising a Aβ displacer may be introduced to the patient to bind to a blood protein, such as albumin, that binds Aβ (for instance, Aβ peptide or non-plaque Aβ) in the patient periphery. Binding of the displacer to the blood protein may facilitate more free Aβ peptide (for instance, Aβ monomers) in the periphery for clearance via natural processes, such as through the liver or kidneys, and/or artificial processes, such as dialysis. Increased removal of the free Aβ peptide in the periphery may ultimately lead to less Aβ peptide in the CNS, which may decrease Aβ plaque formation in Alzheimer's Disease (AD) patients. Other embodiments are described.

9 Claims, 9 Drawing Sheets

Specification includes a Sequence Listing.

(52) U.S. Cl.
CPC ........ *A61M 1/3403* (2014.02); *A61M 1/3413* (2013.01); *A61M 1/342* (2013.01); *A61M 1/362* (2014.02); *A61M 1/3679* (2013.01); *A61M 1/3687* (2013.01); *A61M 1/3431* (2014.02); *A61M 2202/07* (2013.01)

(58) Field of Classification Search
CPC .. A61M 1/3431; A61M 1/3486; A61M 1/362; A61M 1/3679; A61M 1/3687; A61M 2202/07
See application file for complete search history.

(56) References Cited

U.S. PATENT DOCUMENTS

| | | |
|---|---|---|
| 2012/0031840 A1 | 2/2012 | Kitaguchi |
| 2015/0087591 A1 | 3/2015 | Kasinathan |
| 2019/0321537 A1 | 10/2019 | Maheshwari |

OTHER PUBLICATIONS

Choi et al., "Molecular Insights into Human Serum Albumin as a Receptor of Amyloid-β in the Extracellular Region," Journal of the American Chemical Society, 139(43), 15437-15445 (2017) [abstract].

Dennis et al., "Albumin binding as a general strategy for improving the pharmacokinetics of proteins," J Biol Chem. 277(38):35035-43 (2002).

Frejd et al, "Affibody molecules as engineered protein drugs," Exp Mol Med. 49(3):e306 (2017).

Holt et al., "Anti-serum albumin domain antibodies for extending the half-lives of short lived drugs," Protein Eng Des Sel., 21(5):283-8 (2008).

Jacobs et al., "Fusion to a highly stable consensus albumin binding domain allows for tunable pharmacokinetics," Protein Eng Des Sel. 28(10):385-93 (2015).

Levy et al., "Novel exenatide analogs with peptidic albumin binding domains: potent anti-diabetic agents with extended duration of action," PLoS One, 9(2):e87704 (2014); (Deimmunized ABD).

Milojevic et al., "Stoichiometry and affinity of the human serum albumin-Alzheimer's Aβ peptide interactions," Biophysical Journal, 100(1), 183-192 (2011).

O'Connor-Semmes et al. "GSK2374697, a novel albumin-binding domain antibody (AlbudAb), extends systemic exposure of exendin-4: first study in humans-PK/PD and safety," Clin Pharmacol Ther. 96(6):704-12 (2014) [abstract].

Picón-Pagès et al., "Human Albumin Impairs Amyloid β-peptide Fibrillation Through its C-terminus: From docking Modeling to Protection Against Neurotoxicity in Alzheimer's disease," Comput Struct Biotechnol J., 17:963-971 (2019).

Read, Cai et al. "Apelin peptides linked to anti-serum albumin domain antibodies retain affinity in vitro and are efficacious receptor agonists in vivo." Basic & clinical pharmacology & toxicology vol. 126 Suppl 6 (2020): 96-103.

Zorzi et al., "Non-covalent albumin-binding ligands for extending the circulating half-life of small biotherapeutics," Medchemcomm, 10(7):1068-1081 (2019).

International Search Report and Written Opinion for the International Application No. PCT/US2022/053326, mailed Apr. 25, 2023, 16 pages.

| Cargo Type | $\tau_{1/2}$ | Albumin-binding molecule | Conjugate Affinity | $\tau_{1/2}$ | Factor | Ref. |
|---|---|---|---|---|---|---|
| Anti-HER2[§] | 4.3 h (i.v.)[a] | 89D03 (15[b] nM) | n.a. | Single copy: 31.2 h (i.v.)[a] Double copy: 94.5 h (i.v.)[a] | 7[a], 20[a] | 63 |
| huPA inhibitor[†] | 18 min (i.v.)[c] | F-tag (59[b], 220[c], 320[d] nM) | 168[b], 780[c] nM | 7.4 h (i.v.)[c] | 25[c] | 62 |
| hFXIIa inhibitor[†] | 13 min (i.v.)[d] | | 22.4[d], 1600[d] nM | 5.2 h (i.v.)[d] | 24[d] | |
| Fab[‡] | 53 min (i.v.)[d] 24 min (i.v.)[e] | SA21 (467[b], 268[c], 320[d], 7[e] nM) | 320[d] nM | 32.4 h (i.v.)[a] 10.4 h (i.v.)[e] | 37[d] 26[e] | 60 |
| huPA inhibitor[†] | 30 min (i.v.)[e] | | 354[b], 14[e] nM | 24 h (i.v.)[e] | 48[e] | 67 |
| Exendin-4[†] | 30 min (i.v.)[e] | | 610[a], 1560[b], 210[e] nM | 3 d (i.v.)[a] 11 h (i.v.)[e] | 22[e] | 83 |

Indicated terminal half-lives ($\tau_{1/2}$) and related factor of improvement were measured after intravenous (i.v.) or subcutaneous (s.c.) injection for monkey (a), human (b), rat (c), rabbit (d) and mouse (e) species. Indicated albumin-binding affinities were reported as published dissociation constant ($K_d$). Legend: n.a. = not available; † = peptide; § = protein; HER2 = receptor tyrosine-protein kinase erbB-2; huPA = human urokinase-type plasminogen activator; hFXIIa = activated human coagulation factor XII; Fab = antigen-binding fragment.

*FIG. 8*

COMPOUNDS, SYSTEMS, AND TECHNIQUES FOR REMOVAL OF PERIPHERAL AMYLOID BETA PEPTIDE WITH ALBUMIN BINDING COMPETITORS

CROSS-REFERENCE TO RELATED APPLICATION

This application claims the benefit to U.S. Provisional Application No. 63/293,122, filed Dec. 23, 2021, the entire contents of which are incorporated herein by reference in their entirety.

FIELD

The disclosure generally relates to compounds, systems, and/or techniques for increasing the removal of target substances, including amyloid beta (Aβ) (for instance, Aβ peptide), from the blood of a patient using a displacer compound.

STATEMENT REGARDING A SEQUENCE LISTING

The present application contains a sequence listing entitled 8142_0110_SequenceListing.xml created Jan. 27, 2026, which is 20,275 bytes in size. The sequence listing is hereby incorporated by reference in its entirety.

BACKGROUND

Amyloid beta (Aβ) deposition in the central nervous system (CNS) is a hallmark of Alzheimer's disease (AD). The accumulation of Aβ into oligomers and fibrils (for instance, plaques or Aβ plaques) has a key role in the neurodegenerative process and cognitive impairment of AD patients. Therapies have been tested that target Aβ, for example, via eliciting an immune response against beta-amyloid plaques, blocking/dissolving and reducing Aβ protofibril aggregation, or inhibit formation of Aβ precursors. Most conventional therapies have focused on affecting the Aβ levels in the CNS and, more particularly, the cerebrospinal fluid (CSF), with limited effectiveness. Accordingly, AD treatments may benefit from therapies that target other patient systems.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one embodiment, a system may include a reservoir storing a displacer fluid comprising at least one displacer, the displacer fluid may be configured to reduce amyloid beta (Aβ) peptide binding to a blood protein. In some embodiments, Aβ and/or Aβ peptide referred to in the present disclosure may refer to Aβ peptide or other forms of Aβ that are not in the form of plaques (for instance, plaques in the brain, central nervous system, and/or the like, that are considered to be a cause of Alzheimer's disease). In some embodiments, Aβ peptide or non-plaque Aβ may be or may include Aβ monomers and/or oligomers. In various embodiments, the system may further include a fluid circuit for the displacer fluid; a pump device configured to pump the displacer fluid from the reservoir and through the fluid circuit; and a control unit configured to control the operation of the pump device to cause the flow of the displacer fluid through the fluid circuit.

In some embodiments of the system, the fluid circuit may be configured to be fluidically coupled to a circulatory system of a patient.

In various embodiments of the system, the displacer fluid may be configured to increase a clearance of Aβ peptide from a periphery of the patient, the periphery comprising at least one non-central nervous system (CNS) portion of a patient. In some embodiments of the system, increasing the clearance of Aβ peptide may include increasing Aβ peptide monomers in the blood of the patient.

In exemplary embodiments of the system, the blood protein may include albumin.

In some embodiments of the system, the at least one displacer may include one or more of an albumin binding peptide ligand (ABP) or an albumin-binding protein domain (ABD). In various embodiments of the system, the at least one displacer may include at least one of the following: Anti-HER2, huPA inhibitor, jFXHa inhibitor, Fab, Exendin-4, G148-ABD, ABD035, ABD094, and 89D03.

In some embodiments of the system, the system may include a dialysis machine.

In one embodiments, a method of reducing amyloid beta Aβ peptide in a patient may include providing an Aβ displacer to the patient, the Aβ displacer configured to bind with albumin in a periphery of the patient to increase free Aβ peptide in the periphery, and removing the free Aβ peptide from the periphery.

In some embodiments of the method, the Aβ displacer may be configured to increase a clearance of amyloid beta Aβ peptide from the periphery of the patient, the periphery comprising at least one non-central nervous system (CNS) portion of a patient. In various embodiments of the method, the free Aβ peptide may be removed from the periphery via a dialysis machine.

In some embodiments of the method, the Aβ displacer may be provided during a dialysis treatment of the patient. In various embodiments of the method, the Aβ displacer may be provided within dialysate.

In exemplary embodiments of the method, the Aβ displacer may include one or more of an albumin binding peptide ligand (ABP) or an albumin-binding protein domain (ABD). In some embodiments of the method, the Aβ displacer may include at least one of the following: Anti-HER2, huPA inhibitor, jFXHa inhibitor, Fab, Exendin-4, G148-ABD, ABD035, ABD094, and 89D03.

In one embodiment, a method of treating Alzheimer's Disease (AD) may include increasing a clearance of amyloid beta Aβ peptide from a periphery of a patient, the periphery comprising at least one non-central nervous system (CNS) portion of a patient, wherein increasing the clearance of Aβ peptide comprises reducing Aβ peptide binding to albumin in the periphery.

In some embodiments of the method, the displacer may include one or more of an albumin binding peptide ligand (ABP) or an albumin-binding protein domain (ABD). In various embodiments of the method, the displacer may include at least one of the following: Anti-HER2, huPA inhibitor, jFXHa inhibitor, Fab, Exendin-4, G148-ABD, ABD035, ABD094, and 89D03.

In some embodiments of the method, the Aβ displacer may be provided via a dialysis machine. In various embodiments of the method, the Aβ displacer may be provided during a dialysis treatment of the patient.

In one embodiment, a kit may include a reservoir storing a displacer fluid comprising at least one displacer, the displacer fluid configured to reduce amyloid beta Aβ peptide binding to albumin; and an infusion device configured to inject the displacer fluid into a patient.

In some embodiments of the kit, the displacer fluid may be configured to increase a clearance of Aβ peptide from a periphery of the patient, the periphery comprising at least one non-central nervous system (CNS) portion of the patient. In some embodiments of the kit, increasing the clearance of Aβ peptide comprising increasing Aβ peptide monomers in blood of the patient.

In various embodiments of the kit, the at least one displacer may include one or more of an albumin binding peptide ligand (ABP) or an albumin-binding protein domain (ABD). In some embodiments of the kit, the at least one displacer may include at least one of the following: Anti-HER2, huPA inhibitor, jFXHa inhibitor, Fab, Exendin-4, G148-ABD, ABD035, ABD094, and 89D03.

In one embodiment, a method of treating Alzheimer's Disease (AD) may include increasing a clearance of amyloid beta Aβ peptide from a periphery of a patient, the periphery comprising at least one non-central nervous system (CNS) portion of a patient.

In one embodiments, a method of reducing amyloid beta Aβ peptide in a patient may include providing a displacer to a patient, the displacer configured to bind with a blood protein to reduce binding of Aβ peptide to the blood protein.

BRIEF DESCRIPTION OF THE DRAWINGS

By way of example, specific embodiments of the disclosed machine will now be described, with reference to the accompanying drawings, in which:

FIG. 8 illustrates example displacer albumin binding peptides ligands (ABPs) according to some embodiments of the present disclosure.

DETAILED DESCRIPTION

Figure 1:
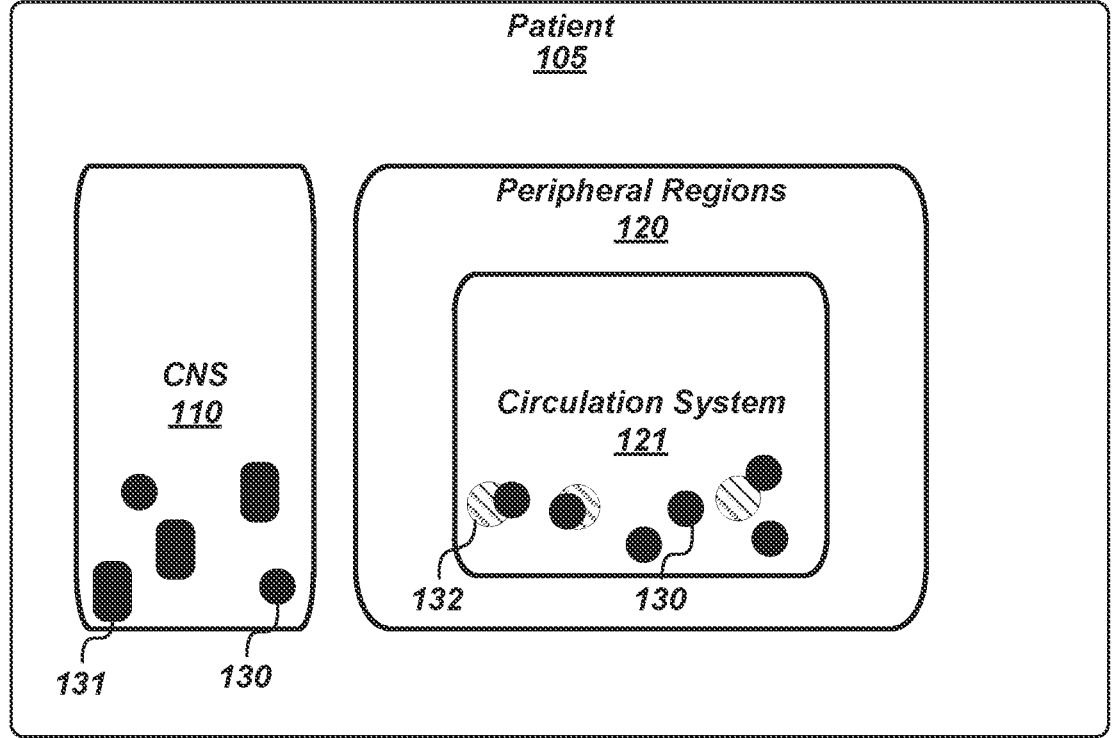
FIG. 1 illustrates a model of a patient.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Various embodiments may generally be directed toward compounds, systems, methods, and/or apparatuses for performing target removal processes for removing protein-bound target substances from patient blood. In some embodiments, the target may be amyloid beta (Aβ). In general, in various embodiments, references to Aβ and/or the removal of Aβ may be or may include removal of Aβ peptide that is not in the form of plaques ("non-plaque Aβ"). In some embodiments, Aβ peptide or non-plaque Aβ may be or may include Aβ monomers and/or oligomers. However, the present disclosure contemplates the removal of Aβ plaques using displacer fluids, processes, techniques, and/or the like according to various embodiments. In exemplary embodiments, the target may be bound to a protein. A non-limiting example of the protein may be or may include albumin. In general, a substance or target substance may be present within patient fluids in a free or unbound form and in a protein-bound form. Conventional clearance processes (for instance, via the liver and/or kidneys) and/or dialysis may be able to remove the target substance in the unbound form, but may not be able (or at least not effectively and/or efficiently able) to remove the target substance in the protein-bound form.

Aβ peptide deposition in the central nervous system (CNS) is a hallmark of Alzheimer's disease (AD). The accumulation of Aβ peptide into oligomers and fibrils (for instance, as plaques or Aβ plaques) has a key role in the neurodegenerative process and cognitive impairment of AD patients. A few emerging therapies targeting Aβ, such as ALZT-OP1, Aducanumab, BAN2401. and CAD106, have been used to treat patients. Other attempts have been made to elicit an immune response against beta-amyloid plaques, block, dissolve, and/or reduce beta-amyloid protofibril aggregation, or inhibit formation of beta-amyloid precursors. Most of these therapies have focused on affecting the Aβ levels in the CNS, including the cerebrospinal fluid (CSF), and have been mainly ineffective.

Accordingly, some embodiments provide compounds, systems, and/or treatment therapies that target periphery removal of Aβ peptide. More specifically, reducing Aβ (e.g., Aβ peptides, non-plaque Aβ, and/or the like) in the periphery (for instance, systems and organs outside of the CNS) may diminish Aβ peptide levels and plaque load in the CNS. An efficient degradation of free Aβ peptide (the fraction of Aβ peptide not bound to plasma proteins, for instance, albumin) outside the CNS may shift the dynamic equilibrium between brain and blood in favor of the blood compartment. Increased peripheral levels of Aβ peptide allows higher subsequent clearance naturally by the liver and/or kidney and/or during a dialysis process. This periphery-based treatment could reduce Aβ peptide accumulation and plaque formation in the CNS. Accordingly, some embodiments may include compounds, systems, and/or techniques to facilitate a periphery-displacer process directed toward the peripheral binding competitors (or displacers) of Aβ peptide to human albumin to reduce bound fraction of Aβ peptide. compounds, systems, and/or techniques to facilitate periphery-displacer therapies according to some embodiments may increase periphery removal of Aβ peptide alone or when coupled with existing treatment strategies.

Compounds, systems, and/or techniques to facilitate periphery-displacer processes according to some embodiments may provide multiple advantages and technical features over conventional systems. One non-limiting example of a technological advantage may include increasing the clearance of Aβ peptide from patient systemic circulation. Another non-limiting technological advantage may include increased displacement of Aβ peptide from human albumin using binding competitors, which may result in higher rates of Aβ peptide elimination through native liver and kidney function and, ultimately, reduced amyloid burden in the CNS.

FIG. 1 illustrates an example patient. As shown in FIG. 1, Aβ 130 (e.g., Aβ peptide or non-plaque Aβ peptide) may be present in a patient 105 in the CNS 110 and peripheral regions 120, such as the circulation system 121. Plaques 131 formed of Aβ peptide 130 may be located in the CNS 110 of an AD patient 105. In the circulation system 121, Aβ peptide 130 may be in a free state or may bound to a protein 132, such as albumin.

Figure 2:
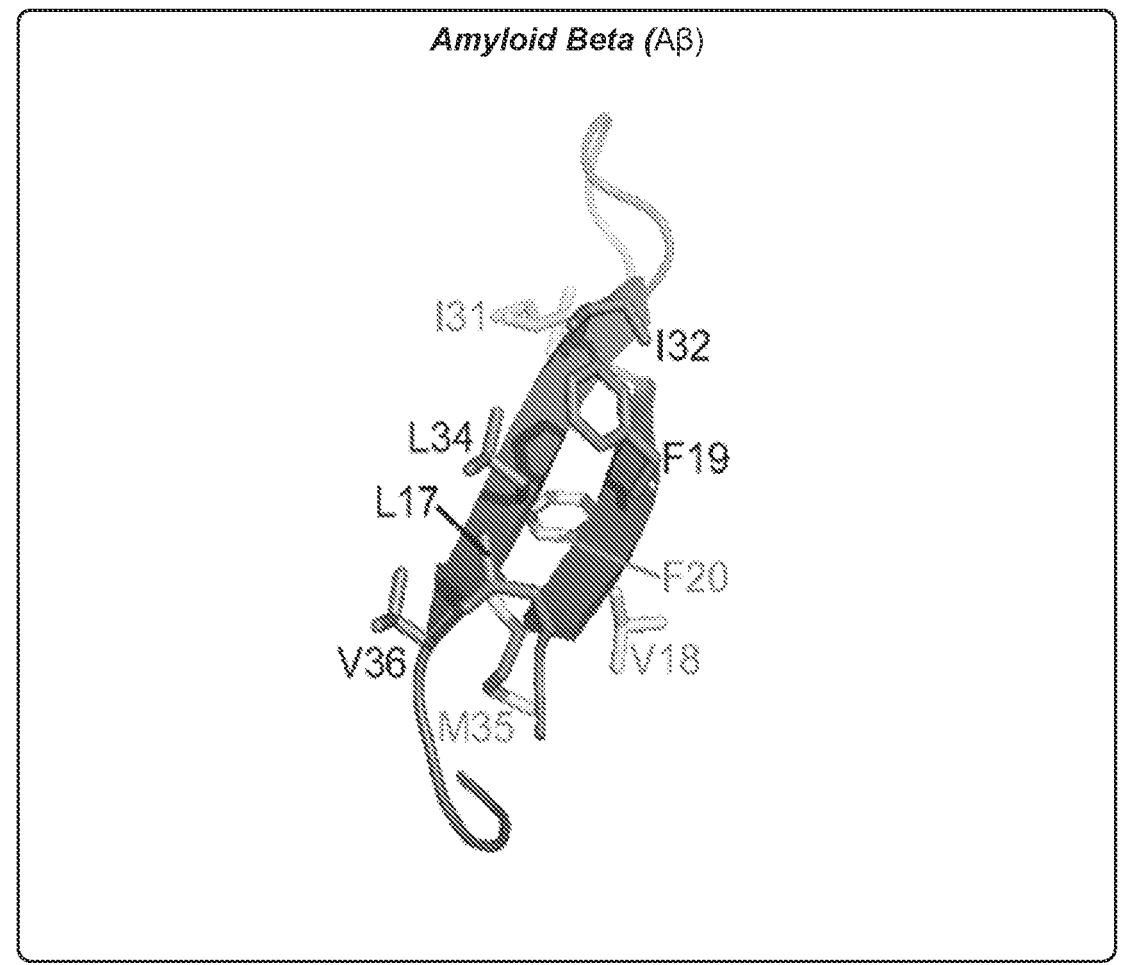
FIG. 2 illustrates an example of an amyloid beta (Aβ) peptide structure.

FIG. 2 illustrates an example of an amyloid beta Aβ peptide structure. Aβ is a peptide composed of 37-49 amino acid residues, with Aβ40 (80-90%) and Aβ42 (5-10%) being the most abundant species. Aβ peptide is found in different forms throughout the body, for instance, as monomers, oligomers, fibrils, and plaques. The fibrillar structure is the primary component deposited in senile plaques found in the extracellular space of the brain of AD patients, mainly in the hippocampus, neocortex, and cerebral vasculature. The abnormal Aβ peptide accumulation is characteristic of AD, which is a common neurodegenerative disease affecting millions of people around the globe. Aβ peptide fibrils are insoluble and built predominantly by Aβ42, which is thought to be more neurotoxic and prone to aggregation due to its hydrophobic and fibrillogenic nature. The production of this peptide occurs through the cleavage of the amyloid precursor protein (APP) by the enzymes β-secretase and γ-secretase. Many cell types throughout the body are capable of producing Aβ peptide, however, its accumulation in the form of plaques is seen in the central nervous system (CNS) only. The formation of Aβ peptide oligomers is an early event in the pathogenesis of AD and levels of soluble oligomers are correlated with disease severity. Soluble oligomeric species are present in both the cerebrospinal fluid (CSF) and plasma.

The majority of Aβ peptide in circulation is bound to plasma proteins, with only a small fraction in a free state (for instance, not bound or otherwise associated with another protein). Albumin is the most abundant protein present in plasma and CSF, with a much lower concentration in CSF due to blood-brain barrier (BBB) selectivity. In this context, albumin plays a key role in the distribution of Aβ peptide in the periphery (i.e., outside of the CNS), including the vascular system, since Aβ peptide is mostly bound to albumin in circulation. Albumin is fundamental for transportation of peptides, drugs, and fatty acids and has been shown to be a receptor for Aβ monomers and soluble oligomers. By releasing Aβ peptide from albumin, shorter elimination half-life of Aβ peptide may occur, for example, according to pharmacokinetics principles.

Accordingly, some embodiments may provide compounds, systems, and/or techniques to facilitate a periphery-displacer process to enable and/or increase Aβ peptide clearance in the periphery, for instance, non-CNS systems (the peripheral "sink hypothesis") to treat or as part of a treatment regimen for AD. A non-limiting example, of a periphery system may be or may include the vascular system.

The efflux of cerebral Aβ peptide across the BBB may occur either through lipoprotein receptor-related protein (LRP) transporters or via the less selective CSF-ISF (interstitial fluid) drainage pathways. In circulation, the clearance of Aβ peptide occurs in hepatic and kidney cells, and this process is mediated mainly by apolipoprotein E (apoE) and low-density lipoprotein receptor-related protein 1 (LPR-1). Blood components also mediate peripheral clearance of Aβ peptide. Secreted enzymes including insulin-degrading enzyme (IDE), neprilysin (NEP) and its homologue endothelinconverting enzyme (ECE), angiotensin converting enzyme (ACE), matrix metalloproteinase-9 (MMP-9), and plasmin, etc., are known collectively as albumin (Ab)-degrading proteases (AbDPs). In addition, monocytes can uptake Aβ peptide from blood and Aβ peptides are captured by erythrocytes via complement receptor 1 and transported to the liver and spleen for clearance.

The concentration of Aβ peptide in the CNS is influenced by vascular Aβ peptide levels. Approximately 40%-60% of brain-derived Aβ peptide is cleared in the periphery. Accordingly, compounds, systems, and/or techniques operative to facilitate periphery-displacer processes according to some embodiments to increase the peripheral removal of Aβ peptide and, therefore, take advantage of the peripheral capacity to clear Aβ peptide, may facilitate the treatment of AD.

The use of binding competitors (or displacers) may be used to increase the removal of protein bound substances. For instance, non-limiting example systems, devices, and methods for increasing the removal of uremic toxins is described in U.S. Pat. Nos. 8,206,591 and 8,419,943 and U.S. Patent Application Publication No. 2019/0321537, the contents of which are each incorporated by reference as if fully set forth herein. For example, compounds (i.e., displacers) and systems may implement a displacer infusion processes for removing a target or deleterious substance bound to a protein in the blood of a patient by introducing a displacer substance into the blood under conditions in which the displacer substance replaces the target substance bound to the protein, thereby resulting in additional unbound deleterious substance in the blood, and removing unbound target substance from the blood by extracorporeal renal replacement treatment. These uremic toxin removal methods utilize displacers which share the same binding site(s) with unwanted toxins to decrease the availability of albumin binding sites, thus increasing the free fractions of these toxins which may be eliminated naturally and/or via dialysis.

Accordingly, some embodiments may provide compounds, systems, and/or techniques for periphery-displacement processes to increase peripheral clearance of Aβ peptide to achieve lower levels of Aβ peptide in CNS based, at least in part, on the sink hypothesis. In various embodiments, periphery-displacement processes may use displacers including, without limitation, albumin binding peptides ligands (ABPs) and albumin-binding protein domains (ABDs).

Figure 3:
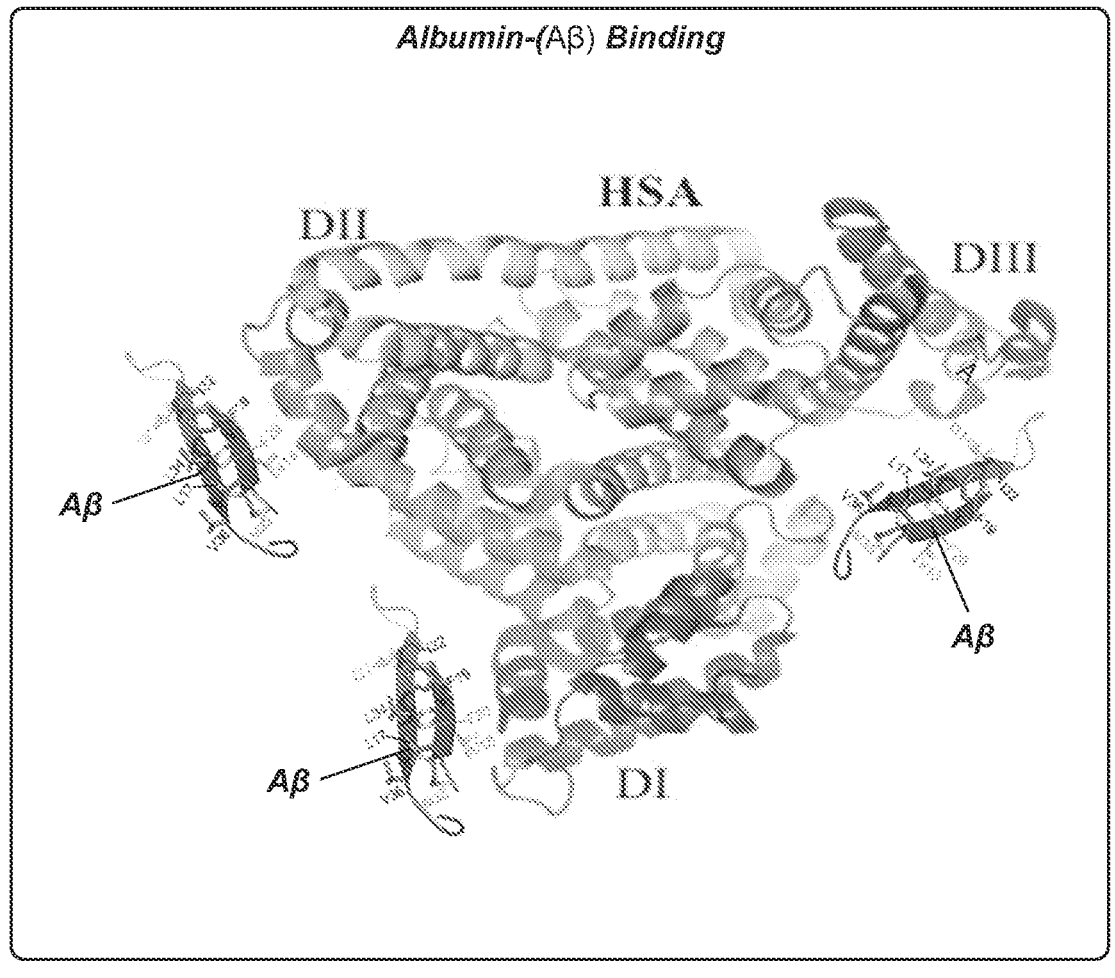
FIG. 3 illustrates an example of a human serum albumin (HSA) protein structure.

FIG. 3 illustrates an example of human serum albumin (HAS) protein structure. As shown in FIG. 3, Aβ peptide may bind to albumin at one or more of binding domain site I (DI), domain site II (DII), or domain site III (DIII). Naturally, albumin is a carrier to not only low molecular weight molecules, but also to peptides and proteins such as insulin, bradykinin, and interferons, and several hundreds of other binders have been identified or predicted. Strategies to prolong peptide and small protein drugs' half-life have been developed and tested. Among these strategies, peptides and small proteins are directly connected to high-affinity binding moieties either recombinantly or chemically during solid-phase synthesis, which non-covalently tether them to the serum proteins after injection, thus impairing their renal filtration. In various embodiments, these albumin-binding peptides (displacers) may not be linked to any drugs, but used as stand-alone substances to occupy albumin binding sites, especially Aβ's albumin binding sites. The ability to bind to albumin may also allow a considerable length of half-life of displacers to function before being cleared out of human body.

ABDs were peptides originally identified as part of cell wall-anchored proteins on Gram-positive bacteria. ABDs target binding site on DII of HSA and do not overlap or interfere with binding to the FcRn-binding site on albumin, which is located in DIII. Several engineered ABDs variants derived from G148-ABD, which is the C-terminal albumin binding domains of Streptococcal protein G, have been extensively studied as a biotechnological tool to improve pharmacokinetics of drugs. For example, the variant ABD035 shows high affinity for human albumin, in the 50-500 fM range. ABD035 is a potential displacer candidate according to some embodiments not only due to the high affinity with albumin, but also due to its high solubility, low aggregation, and suitable biophysical properties. Innate immune recognizes bacterial cell wall components since some are highly specific to immunoglobulin (e.g., protein G of Streptococcus). De-immunized variants, such as ABD094, have no immunogenic potential and is biologically inert, can be candidates of displacers according to some embodiments.

Studies have indicated sequences of peptides with nano-molar affinities to albumin. A non-limiting example may include the 18-amino acids peptide named 89D03 (Ac-WWEQDRDWDFDVFGGGTP-NH2) that binds tightly to human albumin (for instance, with a binding constant of around 15 nM). This high affinity may allow a considerable long resident time on albumin. The chance of Aβ monomer or oligomers' binding to albumin could be compromised when its binding sites are loaded with 89D03. A non-limiting list of illustrative displacer ABPs is included in FIG. 8.

Studies have indicated that Aβ oligomers are recognized by albumin through sites that are evenly partitioned across the three albumin domains and that bind the Ab oligomers with similar dissociation constants in the 1-100 nM range. Albumin DIII has been identified as one of the binding locations of Aβ peptide, for example, that the Cterm (DIII) is a key region of albumin that participates in the inhibition of Aβ peptide assembly and may also facilitate the disassembly of aggregated Aβ peptide, due to its specific Aβ peptide binding capacity.

Interactions between these peptide displacers and Aβ peptide (primarily Aβ1-42 and 1-40 as prototypic molecules) may have an effect on albumin binding. For example, binding of ABDs or ABPs can introduce structural changes of albumin binding to Aβ peptide, even when ABDs and ABPs do binding to the same domains of albumin as Aβ peptide.

Circulating free Aβ peptide exists in heterogeneous forms in plasma, which are primarily monomer and oligomer. Fibril and plaques have not generally been reported in plasma as the free levels of Aβ peptide are low due to albumin binding. Once a substantial amount of free Aβ peptide increases in plasma exceeding their critical levels of self-association, aggregation of Aβ peptide may happen. The kidneys may be able to degrade some degree of Aβ peptide molecules with neprilysin, which is a potent Aβ-degrading enzyme.

Figure 4:
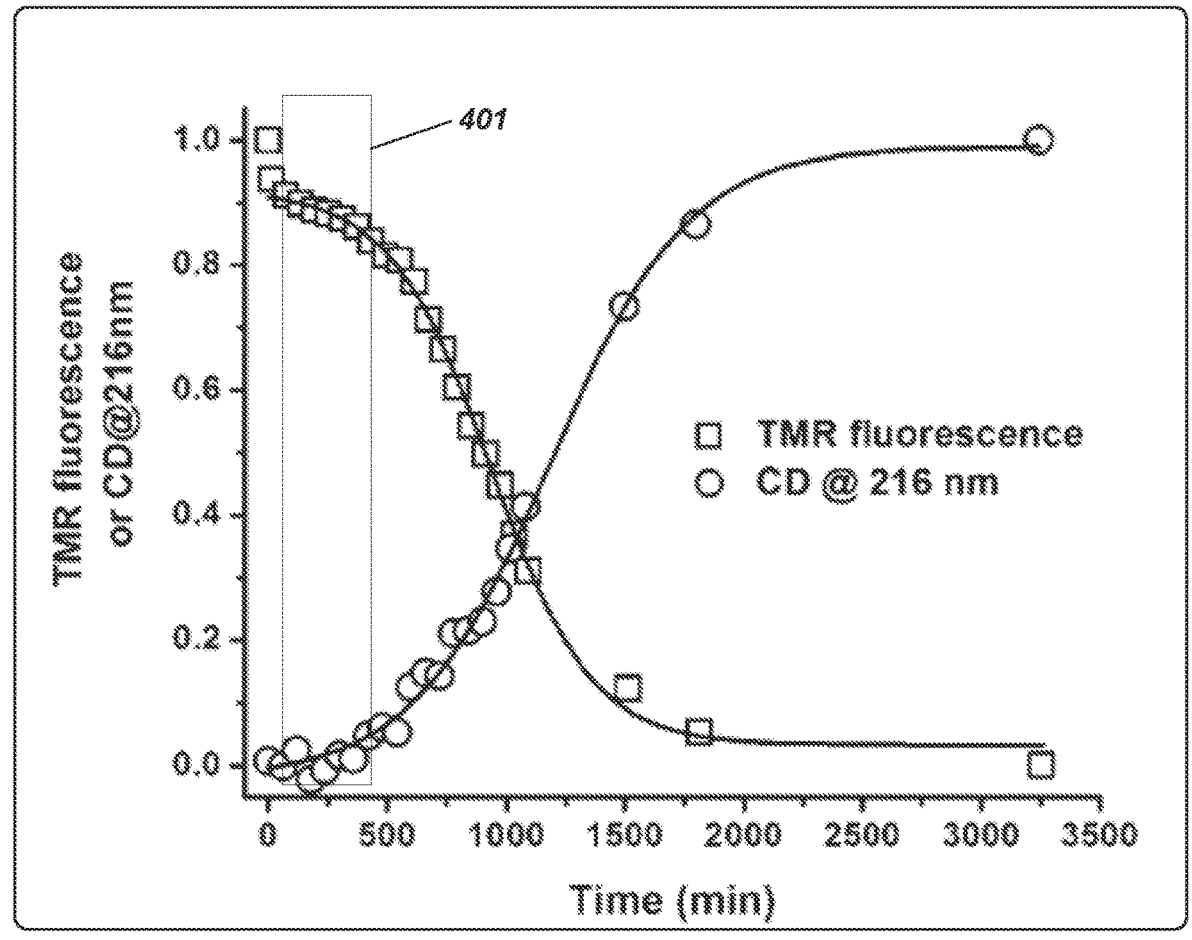
FIG. 4 illustrates an example of Aβ monomer-HSA complexes.
Figure 5:
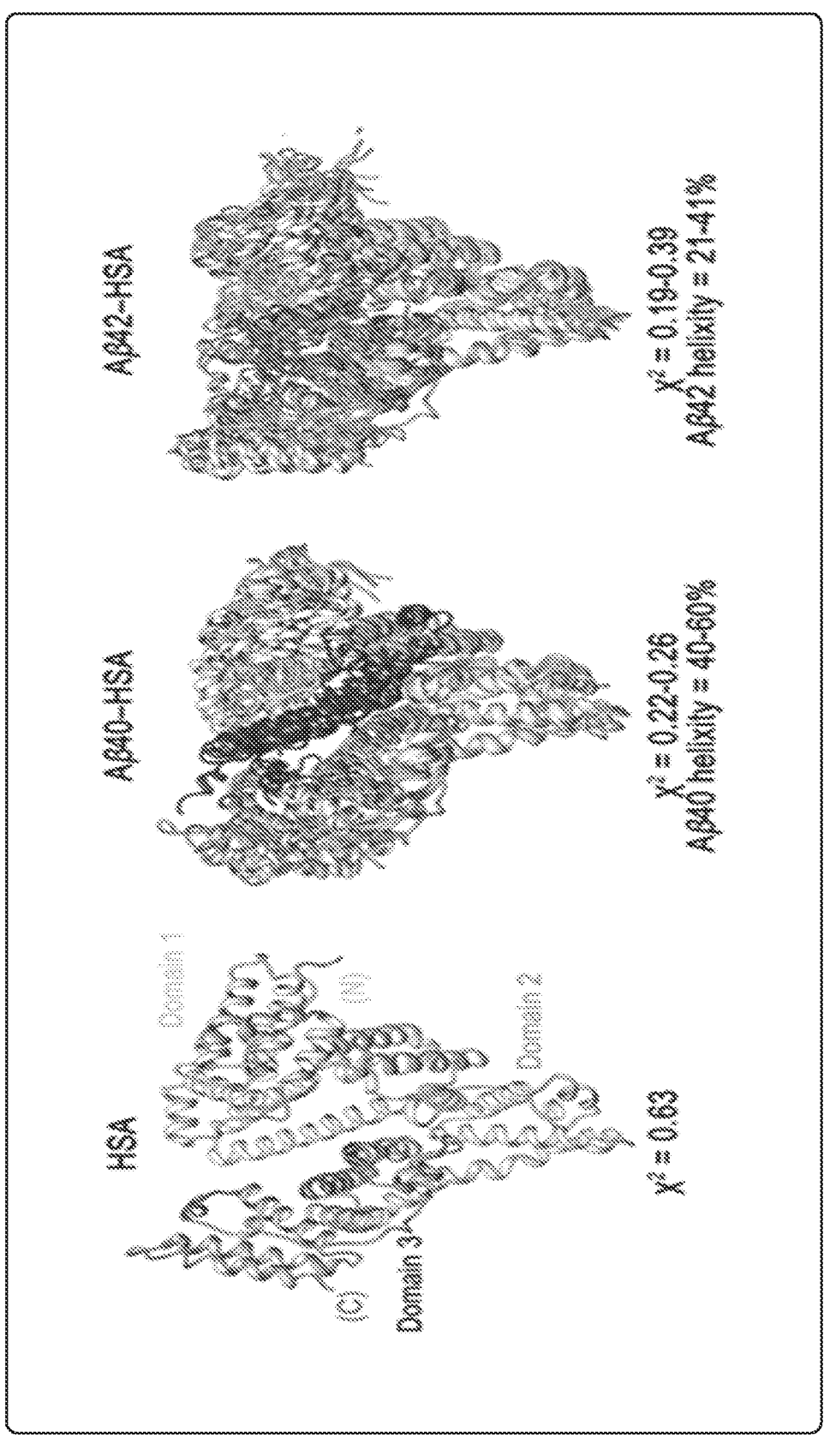
FIG. 5 illustrates a graph of Aβ monomer stability.

Aβ peptide (for instance, Aβ monomers) appear to be stable and could be cleared from circulation before aggregating into larger oligomers or fibrils. FIG. 4 illustrates a graph of Aβ monomer stability. More specifically, FIG. 4 depicts a quantitative analysis of the time course of Aβ oligomerization and subsequent growth steps using tetramethylrhodamine-labeled Aβ. TMR is self-quenching when Aβ peptide aggregates, and CD shows additive fluorescence signals when Aβ peptide aggregates. As indicated in FIG. 5, time area 401 indicates that Aβ monomers are stable for a sufficient amount of time to have displaced Aβ peptide excreted out by the kidney before aggregation.

Aβ peptide enters the brain mainly through receptors for advanced glycation end products (RAGE), a multiligand influx receptor in the immunoglobulin superfamily that is expressed on the luminal surface of brain vessels. Most tested Aβ peptide molecules demonstrating abilities across BBB have been the oligomer form. Some embodiments may provide approaches to manipulate or facilitate free Aβ peptide clearance in a manner favoring fast clearance with minimum or even no re-distribution across the BBB.

The structural characterization of Aβ monomer-HSA complexes has been described in Choi et al., "Molecular Insights into Human Serum Albumin as a Receptor of Amyloid-β in the Extracellular Region," Journal of the American Chemical Society, 139(43), 15437-15445 (2017), the contents of which are incorporated by reference as if fully set forth herein. FIG. 4 illustrates an example of Aβ monomer-HSA complexes as described in Choi et al.

Additional albumin research includes the three-dimensional structures of albumin-binding protein ligands have been described in Zorzi et al., "Non-covalent albumin-binding ligands for extending the circulating half-life of small biotherapeutics," Medchemcomm, 10(7): 1068-1081 (2019); results showing that the albumin oligomers are recognized by albumin through sites that are evenly partitioned across the three albumin domains and that bind the Ab oligomers with similar dissociation constants in the 1-100 nM range have been described in Milojevic et al., "Stoichiometry and affinity of the human serum albumin-Alzheimer's Aβ peptide interactions," Biophysical Journal, 100(1), 183-192 (2011); and results showing that the Cterm (domain 3 or DIII) is a key region of albumin that participates in the inhibition of Aβ peptide assembly and also favors disassembly of already aggregated Aβ peptide, due to its specific Aβ peptide binding capacity, has been described in Picón-Pagès et al., "Human Albumin Impairs Amyloid β-peptide Fibrillation Through its C-terminus: From docking Modeling to Protection Against Neurotoxicity in Alzheimer's disease," Comput Struct Biotechnol J., 17:963-971 (2019); the contents of which are each incorporated by reference as if fully set forth herein.

Incubation of Aβ40 and Aβ42 in the absence of albumin in vitro may result in the formation of Aβ fibers, however, this scenario may be different in vivo, when clearance pathways take place.

In some embodiments, periphery-displacer processes may be used in combination with treatments that facilitate Aβ peptide from the brain. For example, the administration of the monoclonal antibody m266 may facilitate soluble Aβ peptide efflux from the brain, acting as a peripheral sink. The use of combinatory therapies to treat AD has been encouraged given the complexity of the disease, and therapies aiming to increase Aβ peptide efflux combined with improved clearance according to some embodiments may be efficient to treat AD.

Various displacers may be used according to some embodiments. Non-limiting examples of displacers may include albumin binding peptide ligand (ABP); albumin-binding protein domain (ABDs); Anti-HER2; huPA inhibitor; jFXHa inhibitor; Fab, Exendin-4; G148-ABD; ABD035; ABD094; and 89D03.

Non-limiting examples of displacers may also include compounds, such as peptides, described in International Patent Application No. PCT/EP2011/051559 (the '559 Application) (Publication No. WO2011095545), the contents of which are incorporated by reference as if fully set forth herein. An illustrative and non-restrictive example of a compound from the '559 application may include an amino acid sequence that contains: a) an Arg (R) residue, in particular an Arg (R) residue that is capable of forming a hydrogen bond with the amino acid residues Asn (N) 133 & Asn (N) 135 of human serum albumin and/or capable of forming electrostatic interactions with the main-chain oxygen atoms of the Pro (P) 134 and Leu (L) 136 residues of human serum albumin; and/or b) a Trp (W) residue, in particular a Trp (W) residue that is capable of forming electrostatic interactions with the Arg (R) 138 residue of human serum albumin; and/or c) the sequence motif GGG; and preferably at least any two and more preferably all three of (i), (ii) and (iii); and that in addition contain, upstream of said Arg residue, at least one hydrophobic and/or aromatic amino acid residue such that said at least one of said hydrophobic and/or aromatic amino acid residues can bind (in) to a subpocket in (human) serum albumin that comprises (at least) one or more of the following amino acid residues of human serum albumin: V442, S443, T446, L484, L487. H488, K490, T491 and/or V493

Non-limiting examples of displacers may also include compounds SA21 described in Dennis et al., "Albumin binding as a general strategy for improving the pharmacokinetics of proteins," J Biol Chem. 277(38): 35035-43 (2002), the contents of which are incorporated by reference as if fully set forth herein.

Non-limiting examples of displacers may also include ABDs the same or similar to described in the following: (ABD035) Levy et al., "Novel exenatide analogs with peptidic albumin binding domains: potent anti-diabetic agents with extended duration of action," PLOS One, 9(2): e87704 (2014); (Deimmunized ABD) Frejd et al, "Affibody molecules as engineered protein drugs," Exp Mol Med. 49(3):e306 (2017); and (ABDCon) Jacobs et al., "Fusion to a highly stable consensus albumin binding domain allows for tunable pharmacokinetics," Protein Eng Des Sel. 28(10): 385-93 (2015), the contents of each of which are incorporated by reference as if fully set forth herein.

Non-limiting examples of displacers may also include Antibodies anti-HSA domains as described in the following: (AlbudAbs) Holt et al., "Anti-serum albumin domain antibodies for extending the half-lives of short lived drugs," Protein Eng Des Sel., 21(5): 283-8 (2008) and O'Connor-Semmes et al. "GSK2374697, a novel albumin-binding domain antibody (AlbudAb), extends systemic exposure of exendin-4: first study in humans—PK/PD and safety," Clin Pharmacol Ther. 96(6): 704-12 (2014); and Read et al., "Apelin peptides linked to anti-serum albumin domain antibodies retain affinity in vitro and are efficacious receptor agonists in vivo," Basic Clin Pharmacol Toxicol, 1-8 (2019); (CA645) Adams et al., "Extending the half-life of a fab fragment through generation of a humanized anti-human serum albumin Fv domain: An investigation into the correlation between affinity and serum half-life," MAbs. 8(7): 1336-1346 (2016), the contents of each of which are incorporated by reference as if fully set forth herein.

Non-limiting examples of displacers may also include compounds determined via biopanning. In general, biopanning is an affinity selection technique which selects for peptides that bind to a given target. A series of biopanning processes may produce affinity selected ligands binding to a given target, for example, human albumin. A primary structure of the peptide can then be determined, for example, by sequencing the DNA of individual clones of a bacteriophage. Peptide sequences obtained from biopanning using combinatorial peptide libraries have been stored in various databases, including, for example, the biopanning data bank (BDB). By searching sequences binding to albumin through databases, such as BDB, candidate peptide structure can be obtained. The following Table 1 lists potential displacer candidates determined via a search in BDB:

TABLE 1

| Biopanning DataSet ID | SEQ ID | Peptide Sequences | Reference |
|---|---|---|---|
| 1492 | 1 | EVRSFCTDWPAEKSCKPLRG | PMID: 12119302 |
| 1493 | 2 | RAPESFVCYWETICFERSEQ | PMID: 12119302 |
| 1494 | 3 | EMCYFPGICWM | PMID: 12119302 |
| 1690 | 4 | NPFCSWYRWRNWCTK | PMID: 15531628 |
| 1690 | 5 | RHLYCWTWRWCHFKD | PMID: 15531628 |
| 1690 | 6 | SYISTWLNFLFCGQS | PMID: 15531628 |
| 1690 | 7 | NNYSAWLRCLLRAYS | PMID: 15531628 |
| 1787 | 8 | VAWCTIFLCLDV | PMID: 11934284 |
| 1787 | 9 | ADFCEGKDMIDWVYCRLY | PMID: 11934284 |
| 1787 | 10 | FWFCDRIAWYPQHLCEFL | PMID: 11934284 |
| 1787 | 11 | FRNCEPWMLRFGCNPR | PMID: 11934284 |
| 1788 | 12 | FKICDQWFCLMP | PMID: 11934284 |
| 1788 | 13 | HVGCNNALCMQY | PMID: 11934284 |
| 1788 | 14 | WKVCDHFFCLSP | PMID: 11934284 |
| 1788 | 15 | NHGCWHFSCIWD | PMID: 11934284 |
| 1789 | 16 | DWDCVTRWANRDQQCWGP | PMID: 11934284 |
| 1789 | 17 | DWDCVTRWANRDQQCWAL | PMID: 11934284 |
| 1789 | 18 | DWDCVTDWANRHQHCWAL | PMID: 11934284 |
| 1789 | 19 | DWQCVKDWANRRRGCMAD | PMID: 11934284 |
| 1789 | 20 | RNMCKFSWIRSPAFCARA | PMID: 11934284 |
| 2819 | 21 | WQRPSSW | PMID: 25771000 |
| 2819 | 22 | HLYWQRP | PMID: 25771000 |

Displacers according to some embodiments may be used in various concentrations, dosages, and/or the like. In various embodiments, displacers may be used in combination with other displacers and/or other drugs as part of an AD treatment regimen. Embodiments are not limited in this context.

Some embodiments may include processes for validating displacer candidates and investigating their capabilities to compete with Aβ peptide binding to albumin.

Figure 6A:
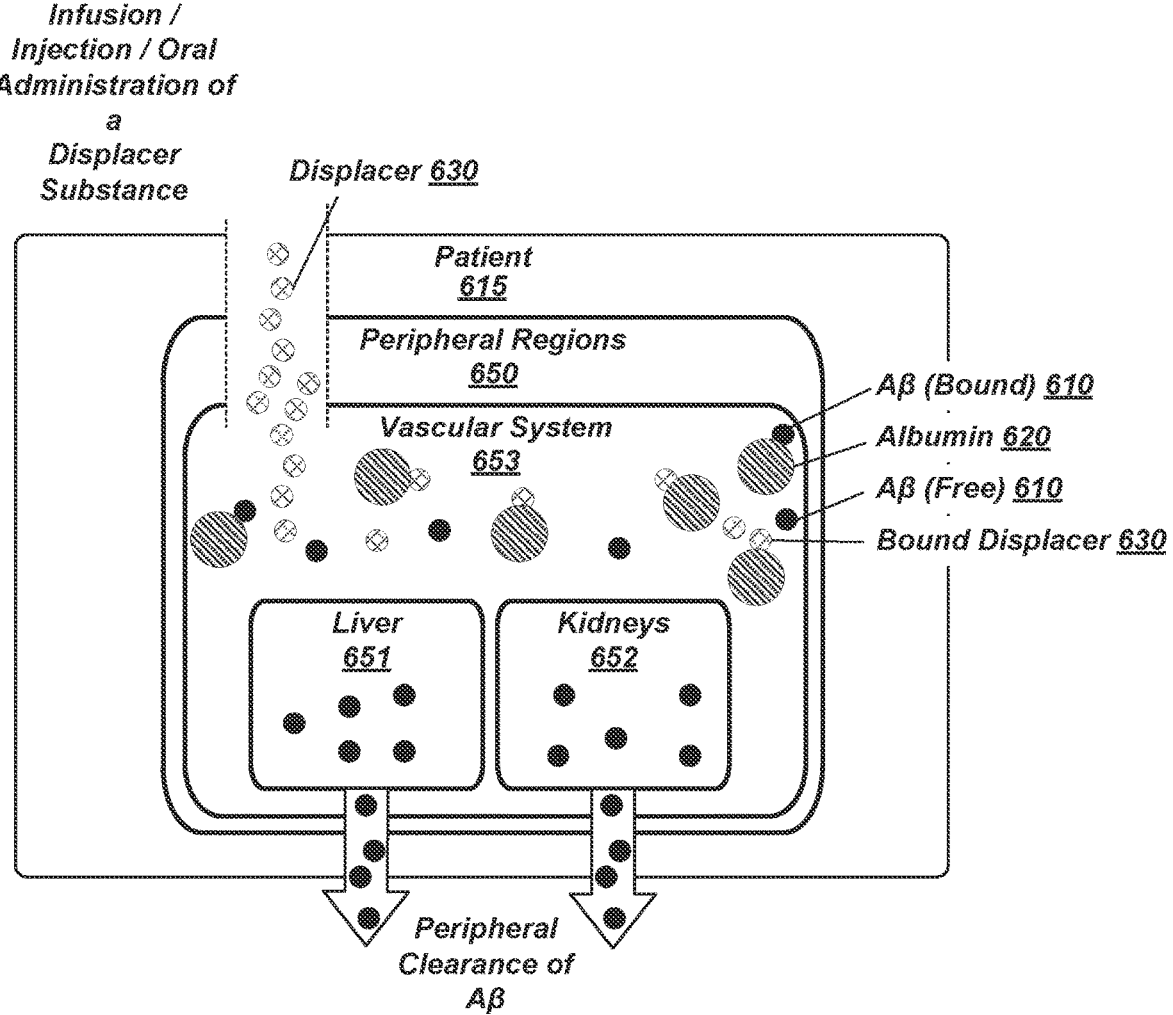
FIG. 6A illustrates an example of a peripheral clearance of Aβ peptide using a displacer according to some embodiments of the present disclosure.

FIG. 6A illustrates an example of a periphery-displacer process for peripheral clearance of Aβ peptide using a displacer according to some embodiments of the present disclosure. As shown in FIG. 6A, a patient 615 may have peripheral regions 650 (for instance, non-brain or non-CNS regions) that include, without limitation, a liver 651, kidneys 652, a vascular system 653, and/or other organs or systems.

Aβ 610 (for instance, Aβ peptide, Aβ monomers, Aβ oligomers, and/or or non-plaque Aβ or Aβ peptide) may be present within peripheral regions 650 in a bound and unbound form. For example, Aβ peptide 610 may be bound to albumin 620. In some embodiments, a periphery-displacer process may include introducing displacer 630 into patient 615, for instance, through an infusion, injection, oral administration, or other process. Displacer 630 may bind to at least a portion of albumin 620 in peripheral regions, leading to less bound Aβ peptide 610 within peripheral regions 650. The unbound Aβ peptide 610 may be cleared naturally, for instance, via the liver 651 and the kidneys 652. The introduction of displacer 630 may lead to an increase of free Aβ peptide 610, which may allow for increased natural clearance of Aβ peptide 610 than would occur without the introduction of displacer 630. The increased natural clearance of Aβ peptide 610 may lead to a decrease in Aβ peptide in the CNS, thereby reducing or eliminating the available Aβ peptide in the CNS to form plaques.

Figure 6B:
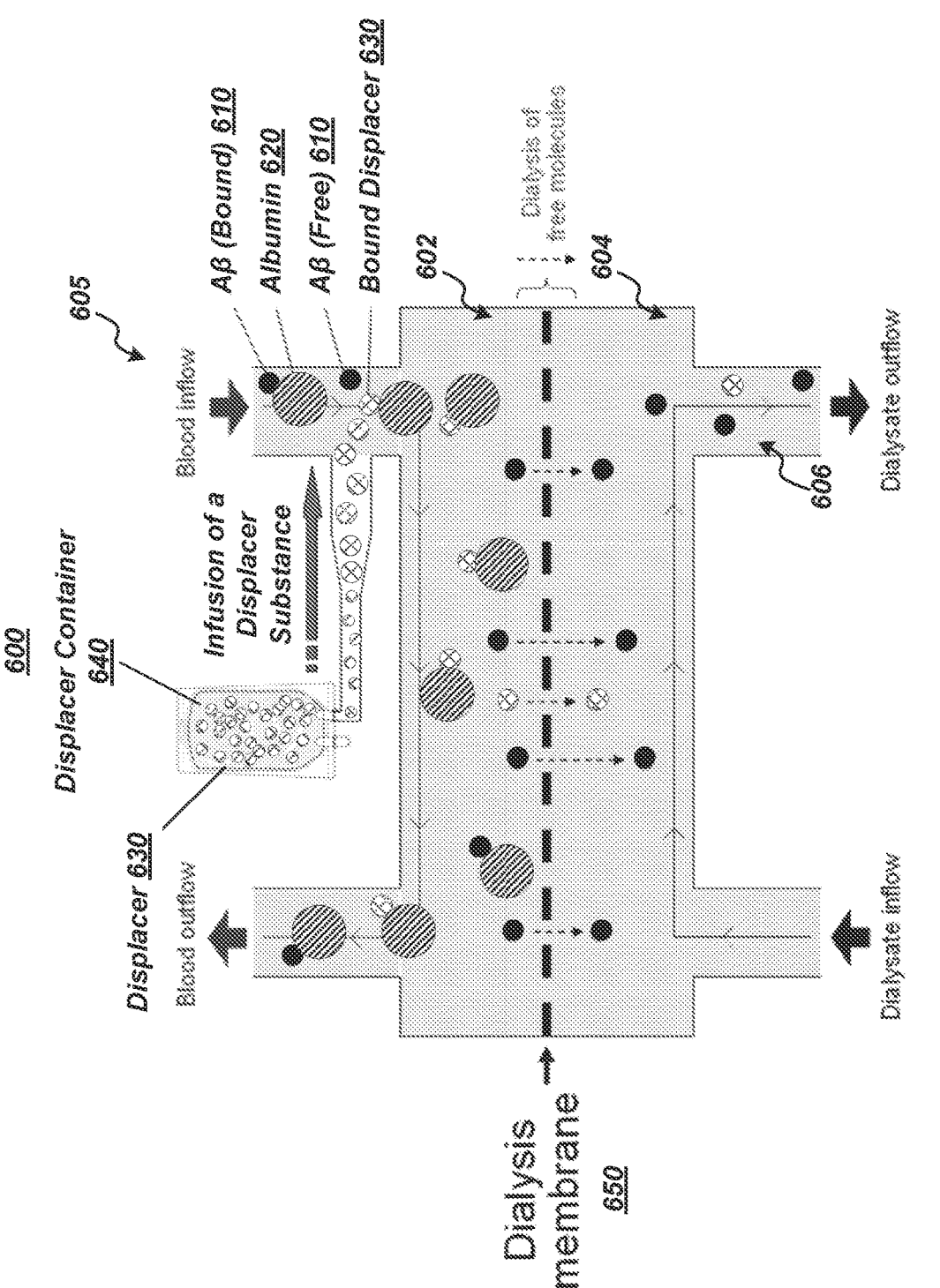
FIG. 6B illustrates an example of dialysis clearance of Aβ peptide using a displacer according to some embodiments of the present disclosure.

FIG. 6B illustrates an example of periphery-displacer process for dialysis clearance of Aβ peptide using a displacer according to some embodiments of the present disclosure. As depicted in FIG. 6B, a dialysis machine 605 may operate to cause a dialysate inflow of a dialysis fluid 604 and a dialysis outflow of the dialysate fluid along with unwanted substances 606. Patient blood 602 may include a target substance in the form of Aβ peptide 610 bound to albumin 620 and free or unbound Aβ peptide 210. Unbound Aβ peptide 210 may cross a dialysis membrane 250 and be removed as an unwanted substance 606 with the dialysate outflow. Bound Aβ peptide 210 is not able to cross dialysis membrane 650 and, therefore, cannot be removed as an unwanted substance 606 with the dialysate outflow.

In some embodiments, dialysis machine 605 may include or may be in fluid communication with a displacer container 640 operative to facilitate the infusion of a displacer 630 into patient blood 602 via a patient blood inflow. As shown in FIG. 6B, displacer 630 may compete for binding sites on albumin 620, leading to a decrease (or even an elimination) of bound Aβ peptide 610 and an increase in free Aβ peptide 610. An increase in free Aβ peptide 610 may facilitate the removal of, or removal of a greater amount of, Aβ peptide 610 from patient blood 602 than could be achieved in the absence of displacer 630.

Figure 7A:
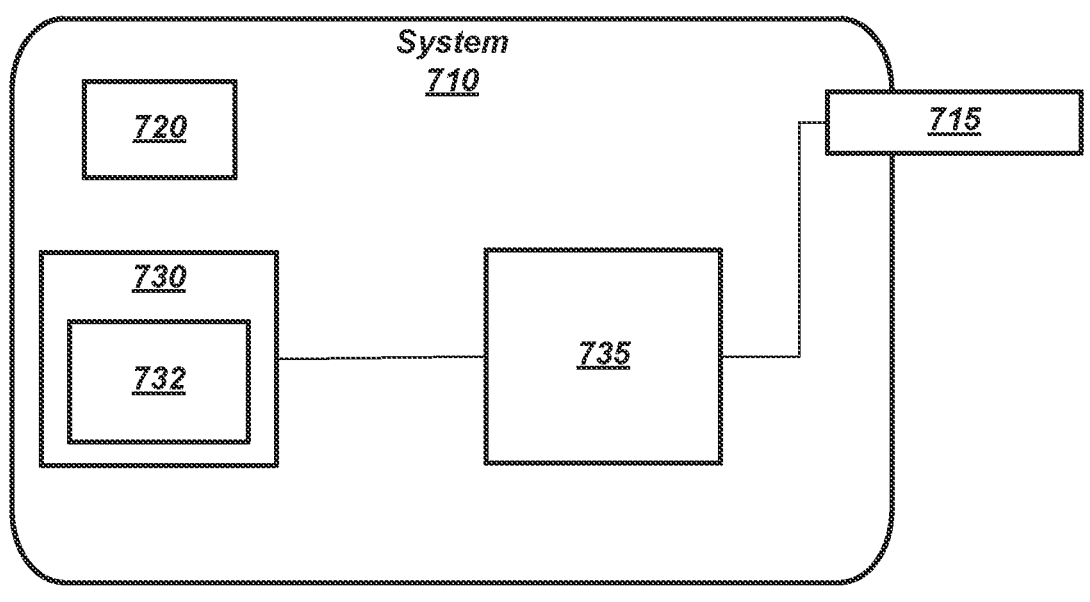
FIG. 7A illustrates an example periphery-displacer process system according to some embodiments of the present disclosure.

FIG. 7A illustrates an example periphery-displacer process system according to some embodiments of the present disclosure. System 710 may be configured to perform a periphery-displacer process according to various embodiments. In some embodiments, system 710 may be or may be a part of a diffusion device or system for flowing a fluid into a patient. In a non-limiting example, system 710 may be or may be a part of a dialysis machine (for instance, dialysis machine 605 of FIG. 6B). System 710 may include a control unit 720 configured to control operational aspects of system 710, such as fluid flow, pumps, valves, and/or the like.

Control unit 720 may be or may include processors, memories, computing devices or elements, logic devices or elements, and/or the like.

System 700 may include a reservoir 730 holding a displacer fluid comprising a displacer ("displacer fluid") 732. In various embodiments, displacer fluid 732 may include a fluid comprising an Aβ peptide displacer according to the present disclosure ("displacer fluid"). In exemplary embodiments, displacer fluid 732 may be combined with other fluids, such as a dialysis fluid (for instance, dialysate). System 700 may include a pump device 735 or other device for causing the flow of displacer fluid 732 into a patient via a patient flow circuit 715. In some embodiments, patient flow circuit 715 may be or may include an extracorporeal circuit for flowing displacer fluid 732 into patient blood.

Figure 7B:
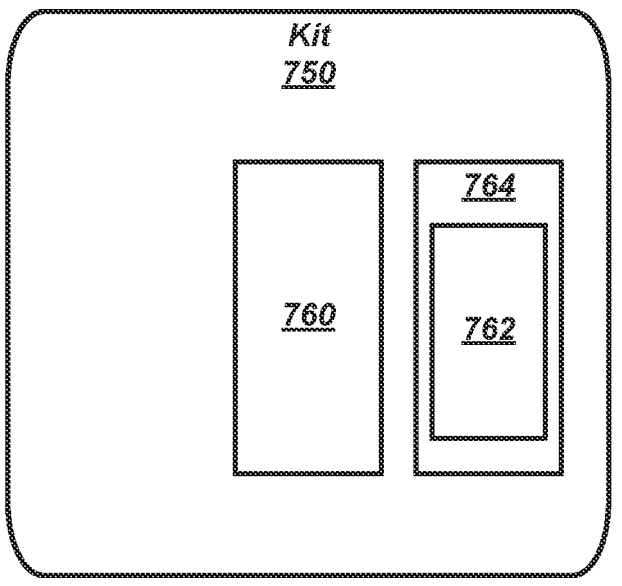
FIG. 7B illustrates an example periphery-displacer process kit according to some embodiments of the present disclosure.

FIG. 7B illustrates an example periphery-displacer process kit according to some embodiments of the present disclosure. Kit 710 may be configured to allow an operator (for instance, a medical professional) to perform a periphery-displacer process according to various embodiments. In some embodiments, kit 710 may include an infusion device 760 and a displacer fluid 762. In some embodiments, kit 710 may be configured with displacer fluid in a separate container 764, such as a bottle. In other embodiments, kit may be configured with displacer fluid 762 within infusion device 760. In various embodiments, displacer fluid 762 may include a fluid comprising an Aβ displacer according to the present disclosure. Infusion device 760 may be or may include a device configured to allow an operator to cause the flow of displacer fluid 762 into a patient. In a non-limiting example, infusion device 760 may include a syringe or similar device.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

```
                          SEQUENCE LISTING

Sequence total quantity: 22
SEQ ID NO: 1              moltype = AA  length = 20
FEATURE                   Location/Qualifiers
source                    1..20
                          mol_type = protein
                          organism = synthetic construct
SEQUENCE: 1
EVRSFCTDWP AEKSCKPLRG                                            20

SEQ ID NO: 2              moltype = AA  length = 20
FEATURE                   Location/Qualifiers
source                    1..20
                          mol_type = protein
                          organism = synthetic construct
SEQUENCE: 2
RAPESFVCYW ETICFERSEQ                                            20

SEQ ID NO: 3              moltype = AA  length = 11
FEATURE                   Location/Qualifiers
source                    1..11
                          mol_type = protein
                          organism = synthetic construct
SEQUENCE: 3
EMCYFPGICW M                                                     11

SEQ ID NO: 4              moltype = AA  length = 15
FEATURE                   Location/Qualifiers
source                    1..15
                          mol_type = protein
                          organism = synthetic construct
SEQUENCE: 4
NPFCSWYRWR NWCTK                                                 15

SEQ ID NO: 5              moltype = AA  length = 15
FEATURE                   Location/Qualifiers
source                    1..15
                          mol_type = protein
                          organism = synthetic construct
SEQUENCE: 5
RHLYCWTWRW CHFKD                                                 15

SEQ ID NO: 6              moltype = AA  length = 15
FEATURE                   Location/Qualifiers
source                    1..15
                          mol_type = protein
                          organism = synthetic construct
SEQUENCE: 6
SYISTWLNFL FCGQS                                                 15

SEQ ID NO: 7              moltype = AA  length = 15
FEATURE                   Location/Qualifiers
source                    1..15
                          mol_type = protein
                          organism = synthetic construct
SEQUENCE: 7
NNYSAWLRCL LRAYS                                                 15

SEQ ID NO: 8              moltype = AA  length = 12
FEATURE                   Location/Qualifiers
source                    1..12
                          mol_type = protein
                          organism = synthetic construct
```

-continued

```
SEQUENCE: 8
VAWCTIFLCL DV                                                            12

SEQ ID NO: 9            moltype = AA  length = 18
FEATURE                 Location/Qualifiers
source                  1..18
                        mol_type = protein
                        organism = synthetic construct
SEQUENCE: 9
ADFCEGKDMI DWVYCRLY                                                      18

SEQ ID NO: 10           moltype = AA  length = 18
FEATURE                 Location/Qualifiers
source                  1..18
                        mol_type = protein
                        organism = synthetic construct
SEQUENCE: 10
FWFCDRIAWY PQHLCEFL                                                      18

SEQ ID NO: 11           moltype = AA  length = 16
FEATURE                 Location/Qualifiers
source                  1..16
                        mol_type = protein
                        organism = synthetic construct
SEQUENCE: 11
FRNCEPWMLR FGCNPR                                                        16

SEQ ID NO: 12           moltype = AA  length = 12
FEATURE                 Location/Qualifiers
source                  1..12
                        mol_type = protein
                        organism = synthetic construct
SEQUENCE: 12
FKICDQWFCL MP                                                            12

SEQ ID NO: 13           moltype = AA  length = 12
FEATURE                 Location/Qualifiers
source                  1..12
                        mol_type = protein
                        organism = synthetic construct
SEQUENCE: 13
HVGCNNALCM QY                                                            12

SEQ ID NO: 14           moltype = AA  length = 12
FEATURE                 Location/Qualifiers
source                  1..12
                        mol_type = protein
                        organism = synthetic construct
SEQUENCE: 14
WKVCDHFFCL SP                                                            12

SEQ ID NO: 15           moltype = AA  length = 12
FEATURE                 Location/Qualifiers
source                  1..12
                        mol_type = protein
                        organism = synthetic construct
SEQUENCE: 15
NHGCWHFSCI WD                                                           12

SEQ ID NO: 16           moltype = AA  length = 18
FEATURE                 Location/Qualifiers
source                  1..18
                        mol_type = protein
                        organism = synthetic construct
SEQUENCE: 16
DWDCVTRWAN RDQQCWGP                                                      18

SEQ ID NO: 17           moltype = AA  length = 18
FEATURE                 Location/Qualifiers
source                  1..18
                        mol_type = protein
                        organism = synthetic construct
SEQUENCE: 17
DWDCVTRWAN RDQQCWAL                                                      18

SEQ ID NO: 18           moltype = AA  length = 18
FEATURE                 Location/Qualifiers
source                  1..18
                        mol_type = protein
```

17 18

-continued

```
                        organism = synthetic construct
SEQUENCE: 18
DWDCVTDWAN RHQHCWAL                                          18

SEQ ID NO: 19          moltype = AA  length = 18
FEATURE                Location/Qualifiers
source                 1..18
                       mol_type = protein
                       organism = synthetic construct
SEQUENCE: 19
DWQCVKDWAN RRRGCMAD                                          18

SEQ ID NO: 20          moltype = AA  length = 18
FEATURE                Location/Qualifiers
source                 1..18
                       mol_type = protein
                       organism = synthetic construct
SEQUENCE: 20
RNMCKFSWIR SPAFCARA                                          18

SEQ ID NO: 21          moltype = AA  length = 7
FEATURE                Location/Qualifiers
source                 1..7
                       mol_type = protein
                       organism = synthetic construct
SEQUENCE: 21
WQRPSSW                                                       7

SEQ ID NO: 22          moltype = AA  length = 7
FEATURE                Location/Qualifiers
source                 1..7
                       mol_type = protein
                       organism = synthetic construct
SEQUENCE: 22
HLYWQRP                                                       7
```

What is claimed is:

1. A system, comprising:
a reservoir storing a displacer fluid comprising at least one displacer, the displacer fluid configured to reduce amyloid beta (Aβ) peptide binding to albumin to increase a concentration of unbound Aβ peptide in a circulatory system of a patient, thereby increasing a clearance of Aβ peptide from a periphery of the patient, the periphery comprising at least one non-central nervous system (CNS) portion of a patient;
a fluid circuit for the displacer fluid;
a pump device configured to pump the displacer fluid from the reservoir and through the fluid circuit; and
a control circuit configured to control the operation of the pump device to cause the flow of the displacer fluid through the fluid unit.

2. The system of claim 1, the fluid circuit configured to be fluidically coupled to the circulatory system of a patient.

3. The system of claim 1, the at least one displacer comprising one or more of an albumin binding peptide ligand (ABP) or an albumin-binding protein domain (ABD).

4. The system of claim 1, the system comprising a dialysis machine.

5. The system of claim 1, the at least one displacer comprising SA21.

6. The system of claim 1, the at least one displacer comprising at least one of the following: albumin-binding protein domain (ABD)035, deimmunized ABD, or ABD-Con.

7. The system of claim 1, the at least one displacer comprising at least one of the following: anti-serum albumin domain antibodies (AlbudAbs), albumin-binding domain antibody (AlbudAb), or CA645.

8. The system of claim 1, wherein the reservoir further includes dialysate.

9. The system of claim 1, wherein the fluid circuit comprises an extracorporeal circuit for flowing the displacer fluid into patient blood.

* * * * *